(12) United States Patent
Ganz

(10) Patent No.: US 9,372,162 B2
(45) Date of Patent: Jun. 21, 2016

(54) CHARACTERIZATION OF SUBTERRANEAN FORMATION PROPERTIES DERIVED FROM QUANTITATIVE X-RAY CT SCANS OF DRILL CUTTINGS

(75) Inventor: Marcus Ganz, Houston, TX (US)

(73) Assignee: Ingrain, Inc., Houston, TX (US)

( * ) Notice: Subject to any disclaimer, the term of this patent is extended or adjusted under 35 U.S.C. 154(b) by 689 days.

(21) Appl. No.: 13/617,184

(22) Filed: Sep. 14, 2012

(65) Prior Publication Data

US 2013/0073207 A1 Mar. 21, 2013

Related U.S. Application Data

(60) Provisional application No. 61/535,601, filed on Sep. 16, 2011.

(51) Int. Cl.
*G01N 23/04* (2006.01)
*G01N 33/24* (2006.01)

(52) U.S. Cl.
CPC .............. *G01N 23/046* (2013.01); *G01N 33/24* (2013.01); *G01N 2223/419* (2013.01); *G01N 2223/423* (2013.01); *G01N 2223/616* (2013.01); *G01N 2223/635* (2013.01)

(58) Field of Classification Search
CPC ............ G01V 5/08; G01V 5/12; G01V 5/125
See application file for complete search history.

(56) References Cited

U.S. PATENT DOCUMENTS

| | | | | |
|---|---|---|---|---|
| 3,409,092 A | * | 11/1968 | Doremus | E21B 21/08 175/50 |
| 5,984,011 A | * | 11/1999 | Misselbrook | E21B 37/00 166/312 |
| 6,009,959 A | * | 1/2000 | Dietzen | B63B 27/20 175/206 |
| 6,349,595 B1 | * | 2/2002 | Civolani | E21B 49/005 73/152.02 |
| 2004/0141583 A1 | * | 7/2004 | Siddiqui | 378/52 |
| 2010/0131204 A1 | * | 5/2010 | Dvorkin | G06T 7/0004 702/6 |
| 2010/0269578 A1 | * | 10/2010 | Detournay et al. | 73/152.11 |

OTHER PUBLICATIONS

Siddiqui, "Techniques for extracting reliable density and porosity data from cuttings.", Society of Petroleum Engineers SPE 96918(2005).*
Shameem Siddiqui, S. P. E., and Aon A. Khamees. "Dual-energy CT-scanning applications in rock characterization.", Society of Petroleum Engineers SPE 90520 (2004).*
VanCleave, Janice, JVC's Science Fun, http://scienceprojectideasforkids.com/2011/floating/, (Sep. 15, 2011).*
Siddiqui, Dual-Energy CT-Scanning Application in Rock Characterization, 2004, Petroleum Engineers Inc.*
Siddiqui, Techniques for Extracting Reliable Density and Porosity Data From Cutting, 2005, Society of Petroleum Engineers.*

(Continued)

*Primary Examiner* — John Breene
*Assistant Examiner* — Raymond Nimox
(74) *Attorney, Agent, or Firm* — Kilyk & Bowersox, P.L.L.C.

(57) ABSTRACT

A method and a system are provided to characterize subterranean formations, which includes extracting drill cuttings from a drilling fluid, and grouping the drill cuttings into a group of cuttings based on a time of arrival of the drill cuttings at the Earth's surface, wherein these steps can be repeated at least once to provide a plurality of groups of drill cuttings that arrive sequentially at different recorded times that correspond to different downhole locations.

28 Claims, 4 Drawing Sheets

(56) References Cited

OTHER PUBLICATIONS

VanCleave, Floating, 2011, JVC'S Science Fun.*
Dvorkin, J. "Digital rock physics bridges scales of measurement." E&P, Rock Physics, Sep. 2009, 3 pages.
International Search Report and Written Opinion issued in corresponding International Patent Application No. PCT/US2012/055405, dated Dec. 18, 2012 (12 pages).
Siddiqui, S., et al., "Dual-Energy CT-Scanning Applications in Rock Characterization," Society of Petroleum Engineers, SPE 90520, Sep. 2004, pp. 1-9.
Wellington, S.L., et al., "X-Ray Computerized Tomography," Journal of Petroleum Technology, 1987, pp. 885-898.
Iovea, M., et al. "A Dedicated On-Board Dual-Energy Computer Tomograph," Journal of Nondestructive Evaluation, vol. 30, No. 3, Jun. 2011, pp. 164-171.

* cited by examiner

CHARACTERIZATION OF SUBTERRANEAN FORMATION PROPERTIES DERIVED FROM QUANTITATIVE X-RAY CT SCANS OF DRILL CUTTINGS

This application claims the benefit under 35 U.S.C. §119 (e) of prior U.S. Provisional Patent Application No. 61/535,601, filed Sep. 16, 2011, which is incorporated in its entirety by reference herein.

BACKGROUND OF THE INVENTION

This invention relates to methods and systems used to characterize subterranean formations.

In order to make effective decisions about drilling and producing hydrocarbons from a subterranean formation, geologists and reservoir engineers attempt to create a static and a dynamic three-dimensional description of an oil or gas reservoir, based on the one- and two-dimensional data from well cores and seismic surveys. The objectives of a static reservoir description include 1) extrapolate core data to uncored wells; 2) define quantity and distribution of rock properties such as porosity, saturation, and permeability in each well; 3) interpolate rock property data between wells; 4) identify flow units from porosity versus permeability populations and 5) build a knowledge base about the reservoir for today and the future. The objectives of a dynamic reservoir description are 1) test the static model for accuracy; 2) predict future performance under various operational scenarios and 3) optimize production for maximum long-term economic return.

Analysis of cores is one method used to obtain static reservoir data. In this method a number of boreholes are drilled over the area of land under which the subterranean formation of interest is located and well cores are extracted. These well cores are then tested and various physical, chemical, electrical, or other properties of the rock and/or fluids are recorded from analysis of the cores. Typically, a well log is stored in a data set in a computer database that can be displayed on a computer display, paper graph or other display medium with the measured physical property of the rock on one axis and depth (distance from the surface) on the other axis. More than one property is typically displayed on the same log.

Analysis of a single core provides information about facies through which the borehole was drilled as a function of depth at the specific surface location of the bore hole. By plotting similar properties over a wide area, the geologist or reservoir engineer can build a three dimensional model of where particular facies exist, make estimates of where hydrocarbons are likely to be present and estimate the quantity of hydrocarbons that can likely be recovered.

Cores may be analyzed in a number of ways. Physical tests may be performed on the core to measure its bulk density for example. Chemical analysis can be performed to estimate effective atomic number. Other laboratory tests can also be performed.

Digital analysis of cores is becoming more common. Dual energy X-ray computed tomographic image scans of cores are used to estimate bulk density and effective atomic number. Plugs extracted from cores are used for further analysis to estimate rock properties such as resistivity, elasticity and permeability and rock/fluid properties such as relative permeability and capillary using digital rock physics techniques.

Using cores to estimate properties of subterranean formations has several shortcomings. Some underground formations such as shales can have many very thin facies, sometimes only a few centimeters thick. The accuracy of core depth estimates is on the order of 3 meters. Boreholes can be horizontally separated by hundreds or thousands meters on the surface. Each borehole provides a point of information about the underground formation at a specific surface location. The geologist must interpolate between borehole locations to estimate the location of a facies of interest in between borehole locations. Underground facies typically do not follow straight lines and as such, significant errors in estimating location of facies can occur. With the advent of horizontal drilling the need to have more detailed information about the precise location of facies and facie properties has become more important. It is not practical to extract horizontal cores from a well bore and vertical cores provide only limited data. Core analysis is not practical in real time or near-real time. Cores must be extracted and shipped to a laboratory for analysis and this can require many days or weeks to complete. As a result, core analysis is of very little value to questions that arise at the time a well is being drilled.

Other techniques are employed to gain insight into wells and subterranean formations. Wire line logs employ a measuring instrument, often called a probe, sonde or logging tool, that is lowered into the borehole on the end of an insulated electrical cable. The cable provides power to operate the downhole instrumentation and additional wires in the cable carry signals from the tool back to the surface. The cable itself is used for estimating depth such that properties measured by the tools can be related to depth in the borehole. Wire line logs are limited because the measurements must be performed down hole and the type and quality of measurements that can be made are limited relative to laboratory tests. To use a wire line log, the drill must be removed from the borehole. Wire line logs have the advantage that they can provide current information about down hole conditions of a well that is being drilled but the need to remove the drill to perform the wire line test delays drilling, often at significant cost.

Mud logs are another technique used to examine well characteristics. Mud logs gather qualitative and semi-quantitative data from hydrocarbon analyzers that measure and record the level of hydrocarbons brought up in the mud. Analyzers such as chromatographs are used to determine the chemical makeup of the hydrocarbons. From the mud analysis, information about the formation can be estimated. In addition to drilling mud, drill cuttings are carried to the surface in the drilling mud. These cuttings can be examined and tested for composition, size, shape, color, texture and hydrocarbon content. Because the mud flows from downhole to the surface and because the drill cuttings must be fluidized in the mud to be returned to the surface, there is a lag time and error in knowing the exact location of the mud and cuttings. Lag times can vary from several minutes to several hours depending upon well conditions. Leaks in the drill pipe or fractures in the well bore can affect lag time introducing additional error in estimating depth from which mud or drill cuttings came. In addition to the error in exact location, drill cuttings are small, typically from about several millimeters to less than 250 microns in size. The small size and uncertainty about the location from which the cutting was produced limit the value of information from analysis of cuttings.

Logging while drilling (LWD) is another technique in which well logging tools are placed downhole as part of the bottom hole assembly (BHA) while the well is being drilled. LWD measurements are somewhat more limited than wire line logs but the cost of LWD is relatively high.

SUMMARY OF THE INVENTION

A feature of the present invention is a method to obtain formation characteristics of comparable quality to digital rock physics in near-real time.

A further feature of the present invention is a system to obtain well and formation characteristics of comparable quality to digital rock physics in near-real time.

A further feature of the present invention is a method to reconstitute a horizontal well core by assembling groups of drill cuttings in a manner that approximates the rock at a specific location in a well bore.

A further feature of the present invention is a method to estimate formation properties by analyzing one or more groups of drill cuttings.

To achieve these and other advantages and in accordance with the purposes of the present invention, as embodied and broadly described herein, the present invention relates, in part, to a method to characterize subterranean formations, comprising: a) extracting drill cuttings from a drilling fluid at the Earth's surface, wherein the drilling fluid transports the drill cuttings to the Earth's surface after use of the drilling fluid in a drilling of a wellbore in a subterranean reservoir; b) grouping the drill cuttings into a group of cuttings based on a time of arrival of the drill cuttings at the Earth's surface; c) repeating steps a) and b) at least once to provide a plurality of groups of drill cuttings that arrive sequentially at different recorded times at the Earth's surface; d) measuring bulk density of at least one of the plurality of groups of drill cuttings of c); e) performing a multi-energy X-ray CT scan of the at least one group of drill cuttings of d) to generate digital images of the drill cuttings of the group of drill cuttings; f) estimating the bulk density and effective atomic number as data pairs for each of the cuttings of the at least one group of cuttings scanned in e); g) assembling a reconstituted core using at least of a portion of the at least one group of drill cuttings; and h) determining at least one rock or formation parameter associated with a subterranean location in the subterranean reservoir using the reconstituted core.

The present invention also relates to a method to characterize subterranean formations, comprising: a) extracting drill cuttings from a used drilling fluid at the Earth's surface, wherein the drilling fluid transports the drill cuttings to the Earth's surface after use of the drilling fluid in a drilling of a wellbore in a subterranean reservoir; b) grouping the drill cuttings into a group of cuttings based on a time of arrival of the drill cuttings at the Earth's surface; c) repeating steps a) and b) at least once to provide a plurality of groups of drill cuttings that arrive sequentially at different recorded times at the Earth's surface; d) measuring bulk density of a plurality of groups of drill cuttings of c); e) performing a multi-energy X-ray CT scan of the plurality of groups of drill cuttings of d) to generate digital images of the drill cuttings of the groups of drill cuttings; f) estimating the bulk density and effective atomic number as data pairs for each of the cuttings of the at least one group of cuttings scanned in e); g) determining if a change in trend occurs for a group of drill cutting in f); h) assembling a reconstituted core using a group of drill cuttings for which a change in trend was determined to occur in g); and i) determining at least one rock or formation parameter associated with a subterranean location in the subterranean reservoir using the reconstituted core of h).

The present invention also relates to a system to characterize subterranean formations, comprising: (a) a drill cutting collection unit for extracting drill cuttings from a drilling fluid in groups of drill cuttings based on a time of arrival of the drill cuttings at the Earth's surface and placing the groups of drill cuttings in respective containers; (b) a device for measuring bulk density of at least one of the plurality of groups of drill cuttings; (c) a multi-energy X-ray CT scanner having a stage capable of holding at least one of the groups of drill cuttings, and optionally including the container that holds the group of drill cuttings, and (d) one or more computer systems operable to i) obtain 3-D digital images of the groups of drill cuttings, ii) estimating the bulk density and effective atomic number as data pairs for each of the cuttings of the at least one group of cuttings scanned in the multi-energy X-ray CT scanner e), iii) assembling a reconstituted core using at least of a portion of the at least one group of drill cuttings, iv) using the reconstituted core to determine at least one rock or formation parameter associated with a subterranean location in the subterranean reservoir, and v) output the results to at least one device to display, print, or store results of the computations; and (e) at least one device to display, print, or store results of the computations.

The present invention also relates to a computer program product on a non-transitory computer readable medium that, when performed on a processor in a computerized device provides a method for performing computations of one or more or all of the indicated steps of the indicated methods.

It is to be understood that both the foregoing general description and following detailed description are exemplary and explanatory only and are intended to provide a further explanation of the present invention, as claimed.

DETAILED DESCRIPTION OF THE PRESENT INVENTION

The present invention relates to a method and system to estimate formation characteristics of comparable quality to digital rock physics in near-real time. A selective grouping and classification of drill cuttings as they are produced in the drilling process can be used as a representation for a horizontal well core and that the representation of the horizontal well core can be analyzed by dual energy X-ray computed tomographic analysis to build a model of the well bore, the region surrounding the well bore and a subterranean reservoir. The method to obtain formation characteristics of comparable quality to digital rock physics in near-real time can involve one or more of the following steps.

Drill cuttings are extracted from a drilling fluid. This can be achieved by means of a shale shaker or similar device.

Figure 1:
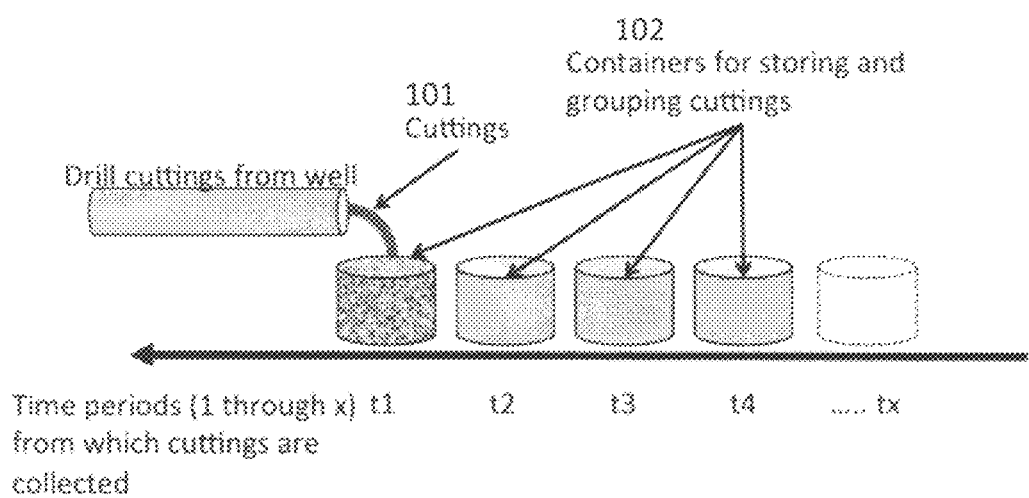
FIG. 1 schematically shows a method for grouping drill cuttings in a process of characterizing subterranean formation properties according to an example of the present application.

The drill cuttings 101 are classified and grouped based on the time they arrive at the surface (see FIG. 1). The drill cuttings can be placed in different containers 102 for storing and/or for the grouping of cuttings based on arrival time and extraction at the Earth's surface. Drill cuttings may be grouped such that the downhole coordinates from which they were produced are estimated to be within about plus or minus 10 feet or more of actual. As used herein, "downhole" refers to the wellbore extending into the subterranean reservoir in a direction or directions further away from its starting point, and not necessarily only vertically down, as the wellbore also can extend horizontally at least in part relative to the Earth's surface which horizontal portion(s) is (are) also considered "downhole" for purposes of the present invention. The grouped drill cuttings may be stored in a bag, canister or similar device for further processing.

Optionally, the drill cuttings may then be further classified by size for example the fraction above about 60 to about 40 mesh or larger or the fraction lower than about 40 to about 60 mesh or smaller.

Optionally, the drill cuttings may be cleaned by washing or similar process and dried.

One group of drill cuttings can be analyzed or two or more groups of drill cuttings can be analyzed and the results arranged in sequential order. The corresponding downhole coordinates of the estimated location of the drill cuttings is recorded along with the physical location of the groups of drill cuttings.

Optionally, the sequential arrangement of grouped drill cuttings may be placed in one or more containers. The container may be a tube with a circular, rectangular or other cross section. The container may be an open tray. The width of the container is selected such that the container and the contained drill cuttings may pass through the sample opening on an X-ray CT scanner or similar device. The width of the container is from about 10 cm or less or from about 8 cm or less or from about 6 cm or less.

Optionally, the grouped, sequential drill cuttings may be secured by embedding them in a material to hold them securely in place. The material for this purpose may be a resin such as epoxy or similar material.

Bulk density of the groups of drill cuttings can be physically measured. One method to do this would be to weigh a group of drill cuttings ($M_1$) and place them in a container of known volume ($V_1$). Then the container is filled with water or another liquid and the volume of liquid required to fill the container is recorded ($V_2$). Bulk density ($\rho$) is then calculated, $$\rho = \frac{M_1}{V_1 - V_2}.$$

An entire bulk density of the group of cuttings placed in container can be determined in this way.

The grouped, sequential drill cuttings (the target object) are then analyzed by a dual energy CT scan. The method of analysis may be as described by Wellington and Vinegar (Wellington, S. L. and Vinegar, H. J., "X-ray Computerized Tomography," JOURNAL OF PETROLEUM TECHNOLOGY, 1987); Siddiqui, A. and Khamees, A. A., "Dual-Energy CT-Scanning Applications in Rock Characterization," SOCIETY OF PETROLEUM ENGINEERS, 2004, SPE 90520; or Derzhi as described in U.S. patent application Ser. No. 13/527,660, filed Jun. 20, 2012, published as U.S. Patent Application Publication No. 2013/0028371 A1, which are incorporated in their entireties by reference herein. The general steps in the method of analysis are but are not limited to
  1. performing a scan (such as a dual energy X-ray CT scan) of the target object,
  2. calculating density and effective atomic number for the target object, based on the high and low energy CT values.

The invention further includes a system, such as a system that includes a computer having a programmable microprocessor, for estimating bulk density and effective atomic number from groupings of selected drill cuttings. The system can include at least an X-ray CT scanner or similar device, a desktop computer with optional equipment such as a high-end video card and at least about 8 GigaBytes (GB) of RAM, 3D analysis software, additional software tools for image segmentation. Sample preparation equipment includes core tools for washing the cuttings, sieves for screening cuttings, holders for the reconstituted core, and similar tools.

The system of the present invention can be mobile or located at a fixed site. The system can be transportable to and from a wellsite where it can be used on-site. The system may be installed in a mobile enclosure, for example, such as a trailer, van, motor coach or similar device such that it can be transported to a well site and analyses run on-site. Thus, with the present invention, the characterization of drill cuttings and ultimately the site of drilling can be studied and understood within minutes or hours of retrieving the drill cuttings and, as indicated, can be done right at the site of the drilling operations, thus providing the operators immediate information with regard to the drilling and well bore operations. With the present invention and the information received within minutes or hours, the drill operators can make adjustments or perfect the drilling or location of drilling operations.

Figure 2:
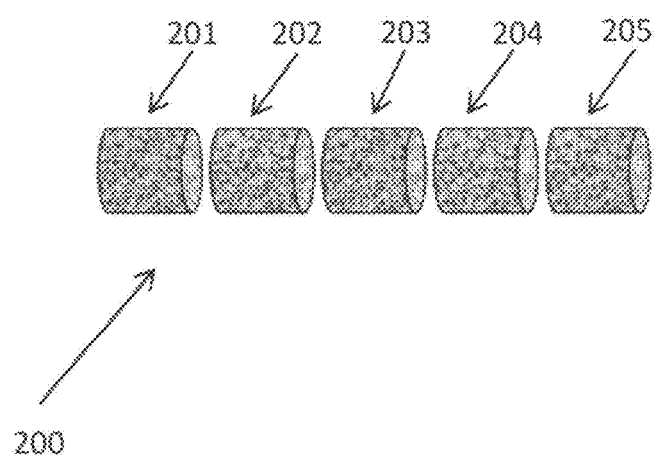
FIG. 2 schematically shows a reconstituted core assembled from grouped drill cuttings according to an example of the present application.

The invention further includes a reconstituted core 200 that comprises drill cuttings that are grouped and classified according to the time at which they arrive at the surface transported by the drilling fluid (see FIG. 2). The groupings of drill cuttings (201, 202, 203, 204, 205, etc.) that comprise the reconstituted core 200 may or may not be physically assembled. The reconstituted core can be a physical assembly or a logical assembly. The cuttings can simulate a core as a three-dimensional value in this way. The reconstituted core cross-references the location on the reconstituted core and the subterranean location from which the drill cuttings were produced. The drill cuttings included in the reconstituted core may include the entire drill cuttings collected in a particular time period and from a particular subterranean location, or the drill cuttings may optionally be further classified according to size and/or shape.

The reconstituted cores can be assembled for every scanned grouped drill cuttings of the extracted sequence for determination of rock or formation properties thereof. This is not required. Multi-energy scans, such as duel-energy scans made for groups of cuttings extracted for regular intervals in the well bore (such as at 10 foot intervals or other distances), can be made on a sequence of grouped drilling cuttings and then the results of estimating the bulk density and effective atomic number as data pairs can be used to monitor for a change in the trend of the results thereof or other change of interest. A change in the trend can be considered to indicate the grouped drill cuttings at the change in trend are representative of a core. The reconstitution of cores and determination of rock or formation properties can be focused on grouped drill cuttings where such a change in trend is observed. This approach can reduce the number grouped drill cuttings requiring further analysis and processing and can provide a focus on the grouped drill cuttings that may represent cores of greater interest.

The X-ray CT scans and estimates of bulk density and effective atomic number produced from the reconstituted cores can be displayed graphically on paper similar to traditional well logs or they can be displayed electronically on a computer. Because the reconstituted core logs are effectively a log of the representation of a horizontal well core, the reconstituted core logs can be used to estimate the porosity and mineralogy along a horizontal well bore. The reconstituted core logs can also be combined with traditional vertical logs to located facies in a formation and to estimate formation properties. The reconstituted cores can also be used to analyze for other rock characteristics and properties such as grain size, grain size variation, pyrite variation, cutting size, cutting size distribution, geomechanics, and other rock properties of interest.

Figure 3:
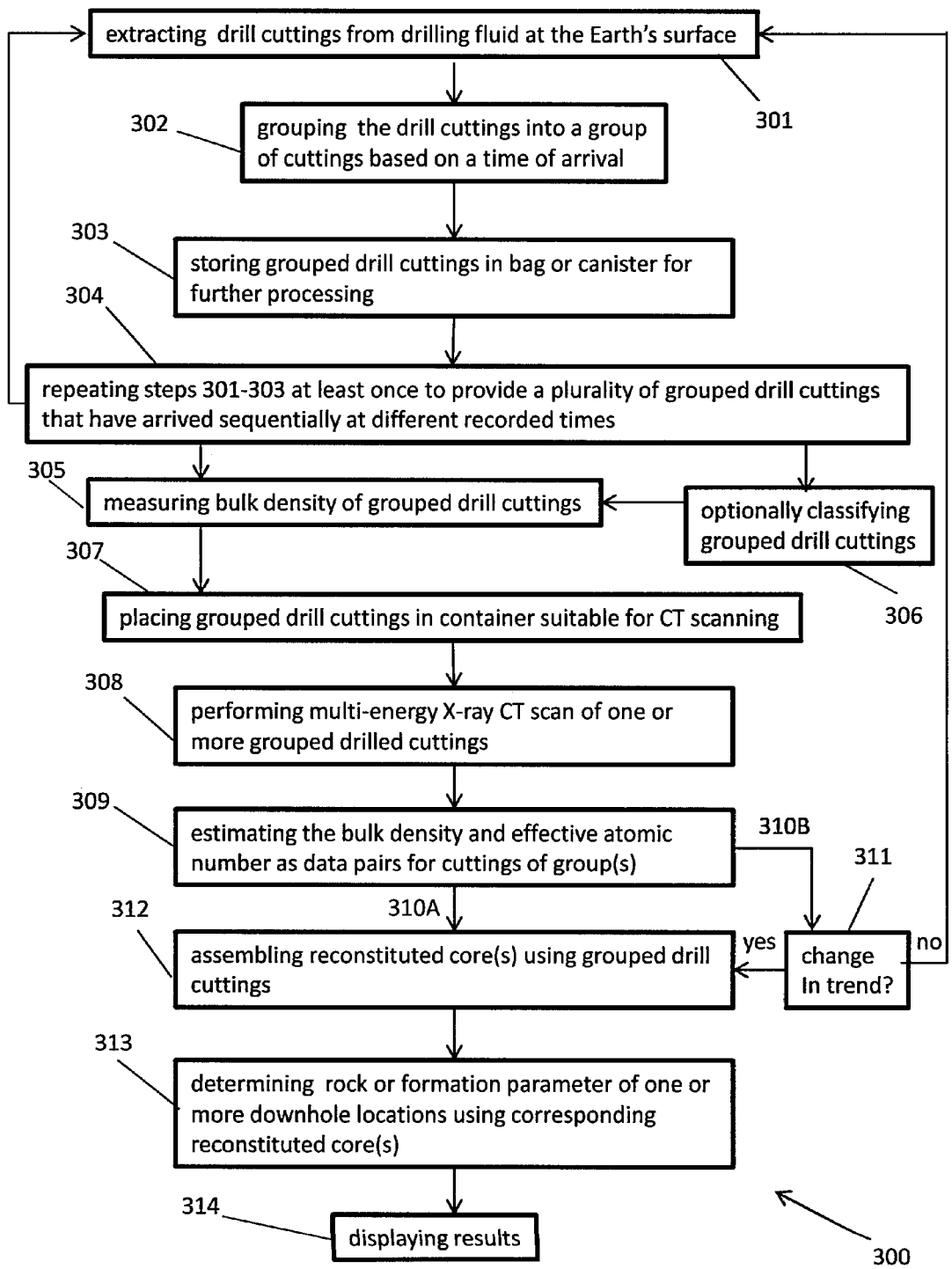
FIG. 3 shows a process of characterizing subterranean formation properties derived from quantitative X-ray CT scan of drill cuttings according to an example of the present application.

Referring to FIG. 3, a process is shown for a process of characterizing subterranean formation properties derived from quantitative X-ray CT scan of drill cuttings which includes steps shown herein. In process (300) illustrated in this figure, for example, steps (301), (302), (303), (304), (305). (306), (307), (308), (309), (310A-B), (311), (312), (313), and (314) are included which are described in further detail elsewhere herein, and reference can be made thereto. For example, as indicated, as one option (310A), reconstituted cores can be assembled for every scanned grouped drill cuttings of the extracted sequence and determining of rock or formation properties can be generated for all or a lesser number thereof. In another option (310B), multi-energy scans, such as duel-energy scans, can be made in step (308) on a sequence of grouped drilling cuttings and then the results of estimating the bulk density and effective atomic number as data pairs in step (309) can be used to monitor, for example, for a change in the trend of the results thereof. A change in the trend can be considered to indicate the grouped drill cuttings at the change in trend are representative of a core. In option (310B), the reconstitution of cores in step (312) and determining of rock or formation properties in step (313) can be focused on grouped drill cuttings where such a change in trend was observed. As indicated, this approach of option (310B) can reduce the number grouped drill cuttings requiring further analysis and processing in steps (312)-(314) and can provide a focus on the grouped drill cuttings that may represent cores of greater interest. In the indicated process, the measured bulk density values indicated herein, such as in step 305 shown in FIG. 3, can be used for calibration and adjustment of estimated density values in the process, such as the estimated density values in step 309. For example, the measured bulk density values indicated herein can be used for calibrating and adjusting estimated density values in the process, such as by using methods shown in the incorporated U.S. patent application Ser. No. 13/527,660, published as U.S. Patent Application Publication No. 2013/0028371 A1. As indicated, these adjustments can be made, for example, as part of step 309 shown in FIG. 3. The measured bulk densities can be used in such methods to compensate for any errors in the interpretation of CT scan data and can produce bulk densities which have lower residual error compared to actual bulk densities and can produce bulk density—effective atomic number trends which are more consistent with physical observations.

Figure 4:
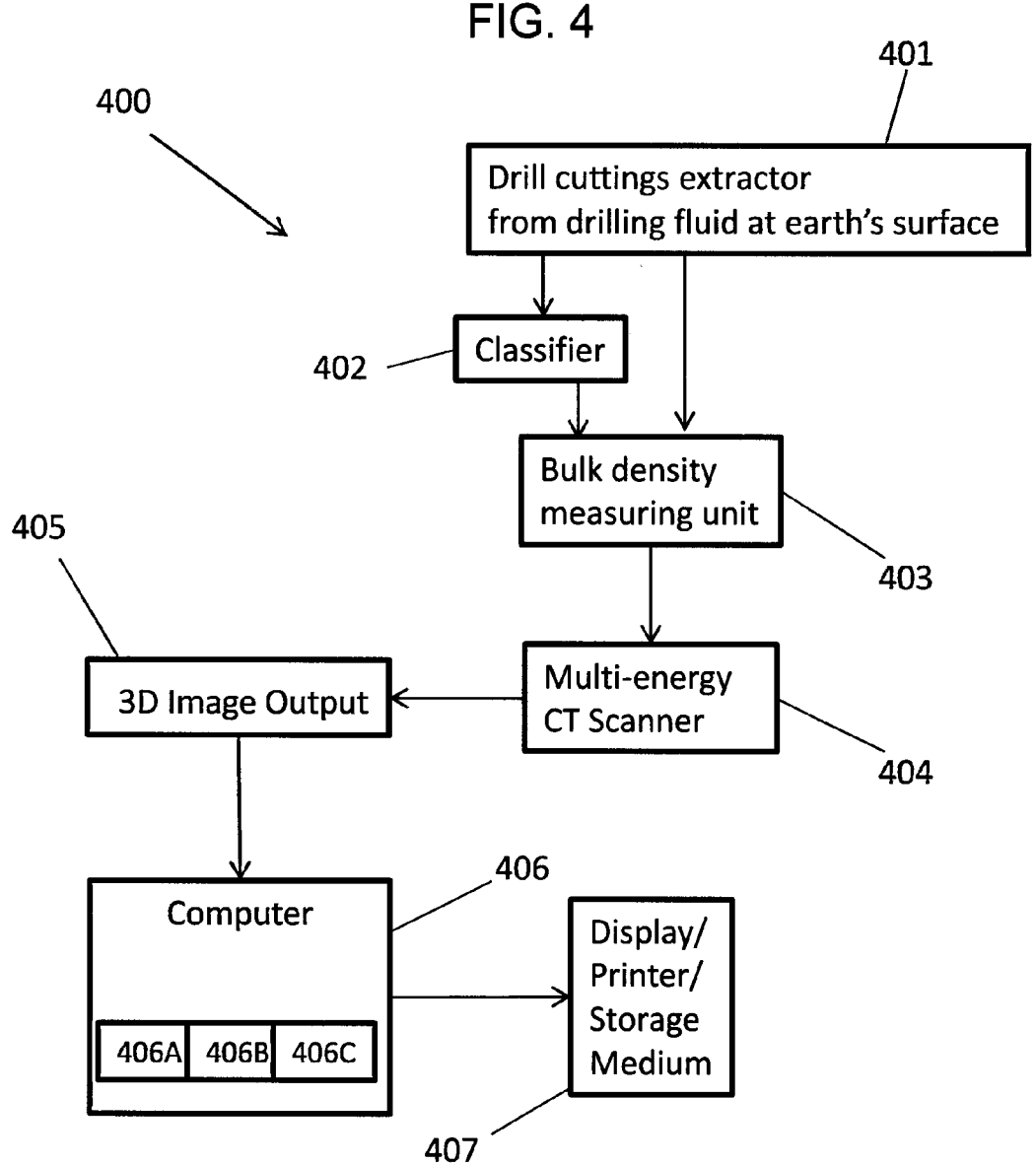
FIG. 4 shows a system which is useful for performing the process of FIG. 3 according to an example of the present application.

Referring to FIG. 4, a system (400) is shown which can be adapted for performing the present methods. As shown in this example, a drill cuttings extractor (401), such as a shale shaker, is used to extract drill cuttings from a drilling fluid. As indicated, these extracted drill cuttings can be grouped based on time of arrival at the surface. A classifier (402) optionally can be used to classify the drill cuttings by size, specific depth interval, or other parameter. As indicated, the classifier can be a stack of mesh sieve trays. A bulk density measuring unit (403), such as the indicated fluid fillable container, can be used in determining the bulk density of the groups of drill cuttings. Three dimensional (3D) images of the grouped drill cuttings can be generated by a multi-energy scanner (404). The scanner can comprise, for example, a dual-energy X-ray multi-energy computer tomographic (CT) scanner, or similar device capable of producing a three dimensional digital image of the drill cuttings. The 3D image output (405) of the scanner can be transferred to a computer (406) having program instructions for carrying out the 3D image analysis, and the indicated estimations of bulk density and effective atomic numbers as data pairs, reconstituted core assembly, and rock or formation parameter determinations, to generate output/results which can transmitted to one or more devices (407), such as a display, a printer, data storage medium, or combinations of these. The computer programs used for 3D image analysis and the CFD computations and simulation modeling can be stored, as a program product, on at least one computer usable storage medium (406B) (e.g. a hard disk, a flash memory device, a compact disc, a magnetic tape/disk, or other media) associated with at least one processor (406A) (e.g., a CPU or GPU) which is adapted to run the programs, or may be stored on an external computer usable storage medium (not shown) which is accessible to the computer processor. Computer (406) can include at least one non-transitory readable memory unit (406C) for storage of the programs, input data and output data, and other program results, or combinations of these. For output display, device (407) can be, for example, a display monitor, CRT, or other visual means of display (not shown). The computer (406) may include one or more system computers, which may be implemented as a single personal computer or as a network of computers. However, those skilled in the art will appreciate that implementations of various techniques described herein may be practiced in a variety of computer system configurations, including hypertext transfer protocol (HTTP) servers, hand-held devices, multiprocessor systems, microprocessor-based or programmable consumer electronics, network PCs, minicomputers, mainframe computers, and the like. The units of system (400) including cuttings extractor (401), classifier (402), bulk density measuring unit (403), scanner (404), computer (406), and output display and/or external data storage (407), can be connected to each other for communications (e.g., data transfer, etc.), via any of hardwire, radio frequency communications, telecommunications, internet connection, or other communication means. It is to be understood that the methods described herein may be implemented in various forms of hardware, software, firmware, special purpose processors, or any combination thereof.

The present invention includes the following aspects/embodiments/features in any order and/or in any combination:

1. The present invention relates to a method to characterize subterranean formations, comprising:

a) extracting drill cuttings from a drilling fluid at the Earth's surface, wherein the drilling fluid transports the drill cuttings to the Earth's surface after use of the drilling fluid in a drilling of a wellbore in a subterranean reservoir;

b) grouping the drill cuttings into a group of cuttings based on a time of arrival of the drill cuttings at the Earth's surface;

c) repeating steps a) and b) at least once to provide a plurality of groups of drill cuttings that arrive sequentially at different recorded times at the Earth's surface;

d) measuring bulk density of at least one of the plurality of groups of drill cuttings of c);

e) performing a multi-energy X-ray CT scan of the at least one group of drill cuttings of d) to generate digital images of the drill cuttings of the group of drill cuttings;

f) estimating the bulk density and effective atomic number as data pairs for each of the cuttings of the at least one group of cuttings scanned in e);

g) assembling a reconstituted core using at least of a portion of the at least one group of drill cuttings; and h) determining at least one rock or formation parameter associated with a subterranean location in the subterranean reservoir using the reconstituted core.

2. The method of any preceding or following embodiment/feature/aspect, further comprising performing steps d), e), f) and g) for at least two of the plurality of groups of drill cuttings of c).

3. The method of any preceding or following embodiment/feature/aspect, wherein b) comprises estimating downhole coordinates from which the group of cuttings were produced to within about plus or minus 10 feet of actual downhole location.

4. The method of any preceding or following embodiment/feature/aspect, wherein said extracting of said drill cuttings from said drilling fluid in a) comprises separating the cuttings from the drilling fluid with a shale shaker.

5. The method of any preceding or following embodiment/feature/aspect, wherein the group of drill cuttings of b) are stored in a bag or canister.

6. The method of any preceding or following embodiment/feature/aspect, further comprising classifying the group of drill cuttings by size after b) and before d).

7. The method of any preceding or following embodiment/feature/aspect, wherein the classifying by size comprises separating and recovering a fraction of the group of drill cuttings having a size above about 60 mesh to about 40 mesh, or a fraction lower than about 40 mesh to about 60 mesh, for further use in d).

8. The method of any preceding or following embodiment/feature/aspect, wherein the group of drill cuttings of b) are cleaned before d).

9. The method of any preceding or following embodiment/feature/aspect, wherein two or more groups of drill cuttings are analyzed in d), e), f) and g), and results thereof are arranged in sequential order.

10. The method of any preceding or following embodiment/feature/aspect, further wherein corresponding downhole coordinates of estimated locations of each of two or more groups of drill cuttings is recorded along with the physical location of the groups of drill cuttings.

11. The method of any preceding or following embodiment/feature/aspect, wherein a sequential arrangement of a plurality of the groups of drill cuttings are placed in separate respective containers.

12. The method of any preceding or following embodiment/feature/aspect, wherein the container is a tube with a circular or rectangular cross section.

13. The method of any preceding or following embodiment/feature/aspect, wherein the container is an open tray having a width selected wherein the container and the contained drill cuttings pass through a sample opening on an X-ray CT scanner in e).

14. The method of any preceding or following embodiment/feature/aspect, where the group of drill cuttings is secured in position in the container by embedding the drill cuttings in a resin material that holds the drill cuttings securely in place.

15. The method of any preceding or following embodiment/feature/aspect, wherein b) comprises physically measuring the bulk density of at least one of the plurality of groups of drill cuttings.

16. The method of any preceding or following embodiment/feature/aspect, wherein the physically measuring comprises weighing a group of drill cuttings ($M_1$) and placing the drill cuttings in a container of known volume ($V_1$), then filling the container with a liquid, and recording volume of liquid ($V_2$) required to fill the container, and calculating bulk density ($\rho$) with the formula:

$$\rho = \frac{M_1}{V_1 - V_2}.$$

17. The method of any preceding or following embodiment/feature/aspect, wherein assembling of the reconstituted core in g) comprises physically assembling the drill cuttings of the group to provide the reconstituted core.

18. The method of any preceding or following embodiment/feature/aspect, wherein assembling of the reconstituted core in g) comprises logically assembling the drill cuttings of the group to provide the reconstituted core.

19. The method of any preceding or following embodiment/feature/aspect, wherein the reconstituted core of g) cross-references a location on the reconstituted core and a subterranean location from which the drill cuttings were produced.

20. The method of any preceding or following embodiment/feature/aspect, wherein the drill cuttings included in the reconstituted core in g) comprise all drill cuttings collected in a particular time period and from a particular subterranean location.

21. The method of any preceding or following embodiment/feature/aspect, wherein the drill cuttings included in the reconstituted core in g) comprise drill cuttings further classified according to size, shape, or both.

22. The method of any preceding or following embodiment/feature/aspect, further comprising i) displaying at least one of the X-ray CT scans and estimates of bulk density and effective atomic number produced from the reconstituted cores.

23. The method of any preceding or following embodiment/feature/aspect, wherein said displaying comprises at least one of graphically displaying on paper and electronically displaying on a computer display.

24. The method of any preceding or following embodiment/feature/aspect, wherein the reconstituted cores are displayed as a log of a representation of a horizontal well core.

25. The method of any preceding or following embodiment/feature/aspect, wherein the at least one rock or formation parameter associated with a subterranean location in the subterranean reservoir of h) is at least one rock property selected from porosity, mineralogy, grain size, grain size variation, pyrite variation, cutting size, cutting size distribution, geomechanics, or any combinations thereof.

26. The method of any preceding or following embodiment/feature/aspect, wherein the at least one rock or formation parameter associated with a subterranean location in the subterranean reservoir of h) is at least one of a facies location in the formation and a formation property.

27. The present invention also relates to a method to characterize subterranean formations, comprising:

a) extracting drill cuttings from a used drilling fluid at the Earth's surface, wherein the drilling fluid transports the drill cuttings to the Earth's surface after use of the drilling fluid in a drilling of a wellbore in a subterranean reservoir;

b) grouping the drill cuttings into a group of cuttings based on a time of arrival of the drill cuttings at the Earth's surface;

c) repeating steps a) and b) at least once to provide a plurality of groups of drill cuttings that arrive sequentially at different recorded times at the Earth's surface;

d) measuring bulk density of a plurality of groups of drill cuttings of c);

e) performing a multi-energy X-ray CT scan of the plurality of drill cuttings of d) to generate digital images of the drill cuttings of the groups of drill cuttings;

f) estimating the bulk density and effective atomic number as data pairs for each of the cuttings of the at least one group of cuttings scanned in e);

g) determining if a change in trend occurs for a group of drill cutting in f):

h) assembling a reconstituted core using a group of drill cuttings for which a change in trend was determined to occur in g); and i) determining at least one rock or formation parameter associated with a subterranean location in the subterranean reservoir using the reconstituted core of h).

28. A system to characterize subterranean formations, comprising:
- (a) a drill cutting collection unit for extracting drill cuttings from a drilling fluid in groups of drill cuttings based on a time of arrival of the drill cuttings at the Earth's surface and placing the groups of drill cuttings in respective containers;
- (b) a device for measuring bulk density of at least one of the plurality of groups of drill cuttings;
- (c) a multi-energy X-ray CT scanner having a stage capable of holding at least one of the groups of drill cuttings, and optionally including the container that holds the group of drill cuttings, and
- (d) one or more computer systems operable to i) obtain 3-D digital images of the groups of drill cuttings, ii) estimating the bulk density and effective atomic number as data pairs for each of the cuttings of the at least one group of cuttings scanned in the multi-energy X-ray CT scanner e), iii) assembling a reconstituted core using at least of a portion of the at least one group of drill cuttings, iv) using the reconstituted core to determine at least one rock or formation parameter associated with a subterranean location in the subterranean reservoir, and v) output the results to at least one device to display, print, or store results of the computations; and
- (e) at least one device to display, print, or store results of the computations.

29. The present invention also relates to a computer program product on a non-transitory computer readable medium that, when performed on a processor in a computerized device provides a method for performing computations of one or more or all of the indicated steps of any preceding method.

The present invention can include any combination of these various features or embodiments above and/or below as set forth in sentences and/or paragraphs. Any combination of disclosed features herein is considered part of the present invention and no limitation is intended with respect to combinable features.

Applicant specifically incorporates the entire contents of all cited references in this disclosure. Further, when an amount, concentration, or other value or parameter is given as either a range, preferred range, or a list of upper preferable values and lower preferable values, this is to be understood as specifically disclosing all ranges formed from any pair of any upper range limit or preferred value and any lower range limit or preferred value, regardless of whether ranges are separately disclosed. Where a range of numerical values is recited herein, unless otherwise stated, the range is intended to include the endpoints thereof, and all integers and fractions within the range. It is not intended that the scope of the invention be limited to the specific values recited when defining a range.

Other embodiments of the present invention will be apparent to those skilled in the art from consideration of the present specification and practice of the present invention disclosed herein. It is intended that the present specification and examples be considered as exemplary only with a true scope and spirit of the invention being indicated by the following claims and equivalents thereof.

What is claimed is:

1. A method to characterize subterranean formations, comprising:
- a) extracting drill cuttings from a used drilling fluid at the Earth's surface, wherein the drilling fluid transports the drill cuttings to the Earth's surface after use of the drilling fluid in a drilling of a wellbore in a subterranean reservoir;
- b) grouping the drill cuttings into a group of cuttings based on a time of arrival of the drill cuttings at the Earth's surface;
- c) repeating steps a) and b) at least once to provide a plurality of groups of drill cuttings that arrive sequentially at different recorded times at the Earth's surface, wherein the plurality of groups of drill cuttings are placed in separate respective containers in a sequential arrangement thereof, wherein different containers are used to store different groups of drill cuttings having different times of arrival;
- d) measuring a bulk density of at least one of the plurality of groups of drill cuttings of c) to provide a measured bulk density;
- e) performing a multi-energy X-ray CT scan of the at least one group of drill cuttings of d) to generate digital images of the drill cuttings of the group of drill cuttings;
- f) estimating an estimated bulk density and effective atomic number as data pairs for each of the cuttings of the at least one group of cuttings scanned in e), wherein the estimating of the estimated bulk density further comprises using the measured bulk density measured in step d) in calibrating and adjusting estimated density values determined for the cuttings of the at least one group of cuttings scanned in e);
- g) assembling a reconstituted core using at least of a portion of the at least one group of drill cuttings; and
- h) determining at least one rock or formation parameter associated with a subterranean location in the subterranean reservoir using the reconstituted core.

2. The method of claim 1, further comprising performing steps d), e), f) and g) for at least two of the plurality of groups of drill cuttings of c).

3. The method of claim 1, wherein b) comprises estimating downhole coordinates from which the group of cuttings were produced to within about plus or minus 10 feet of actual downhole location.

4. The method of claim 1, wherein said extracting of said drill cuttings from said drilling fluid in a) comprises separating the cuttings from the drilling fluid with a shale shaker.

5. The method of claim 1, wherein the group of drill cuttings of b) are stored in a bag or canister.

6. The method of claim 1, further comprising classifying the group of drill cuttings by size after b) and before d).

7. The method of claim 6, wherein the classifying by size comprises separating and recovering a fraction of the group of drill cuttings having a size above about 60 mesh to about 40 mesh, or a fraction lower than about 40 mesh to about 60 mesh, for further use in d).

8. The method of claim 1, wherein the group of drill cuttings of b) are cleaned before d).

9. The method of claim 1, wherein two or more groups of drill cuttings are analyzed in d), e), f) and g), and results thereof are arranged in sequential order.

10. The method of claim 9, further wherein corresponding downhole coordinates of estimated locations of each of two or more groups of drill cuttings is recorded along with the physical location of the groups of drill cuttings.

11. The method of claim 1, wherein the container is a tube with a circular or rectangular cross section.

12. The method of claim 1, wherein the container is an open tray having a width selected wherein the container and the contained drill cuttings pass through a sample opening on an X-ray CT scanner in e).

13. The method of claim 1, where the group of drill cuttings is secured in position in the container by embedding the drill cuttings in a resin material that holds the drill cuttings securely in place.

14. The method of claim 1, wherein d) comprises physically measuring the bulk density of at least one of the plurality of groups of drill cuttings.

15. The method of claim 14, wherein the physically measuring comprises weighing a group of drill cuttings ($M_1$) and placing the drill cuttings in a container of known volume ($V_1$), then filling the container with a liquid, and recording volume of liquid ($V_2$) required to fill the container, and calculating bulk density ($\rho$) with the formula:

$$\rho = \frac{M_1}{V_1 - V_2}.$$

16. The method of claim 1, wherein assembling of the reconstituted core in g) comprises physically assembling the drill cuttings of the group to provide the reconstituted core.

17. The method of claim 1, wherein assembling of the reconstituted core in g) comprises logically assembling the drill cuttings of the group to provide the reconstituted core.

18. The method of claim 1, wherein the reconstituted core of g) cross-references a location on the reconstituted core and a subterranean location from which the drill cuttings were produced.

19. The method of claim 1, wherein the drill cuttings included in the reconstituted core in g) comprise all drill cuttings collected in a particular time period and from a particular subterranean location.

20. The method of claim 19, wherein the drill cuttings included in the reconstituted core in g) comprise drill cuttings further classified according to size, shape, or both.

21. The method of claim 1, further comprising i) displaying at least one of the X-ray CT scans and estimates of bulk density and effective atomic number produced from the reconstituted cores.

22. The method of claim 21, wherein said displaying comprises at least one of graphically displaying on paper and electronically displaying on a computer display.

23. The method of claim 21, wherein the reconstituted cores are a representation of a horizontal well core.

24. The method of claim 1, wherein the at least one rock or formation parameter associated with a subterranean location in the subterranean reservoir of h) is at least one rock property selected from porosity, mineralogy, grain size, grain size variation, pyrite variation, cutting size, cutting size distribution, geomechanics, or any combinations thereof.

25. The method of claim 1, wherein the at least one rock or formation parameter associated with a subterranean location in the subterranean reservoir of h) is at least one of a facies location in the formation and a formation property.

26. A method to characterize subterranean formations, comprising:
   a) extracting drill cuttings from a used drilling fluid at the Earth's surface, wherein the drilling fluid transports the drill cuttings to the Earth's surface after use of the drilling fluid in a drilling of a wellbore in a subterranean reservoir;
   b) grouping the drill cuttings into a group of cuttings based on a time of arrival of the drill cuttings at the Earth's surface;
   c) repeating steps a) and b) at least once to provide a plurality of groups of drill cuttings that arrive sequentially at different recorded times at the Earth's surface, wherein the plurality of groups of drill cuttings are placed in separate respective containers in a sequential arrangement thereof, wherein different containers are used to store different groups of drill cuttings having different times of arrival;
   d) measuring a bulk density of a plurality of groups of drill cuttings of c) to provide a measured bulk density;
   e) performing a multi-energy X-ray CT scan of the plurality of drill cuttings of d) to generate digital images of the drill cuttings of the groups of drill cuttings;
   f) estimating an estimated bulk density and effective atomic number as data pairs for each of the cuttings of the at least one group of cuttings scanned in e), wherein the estimating of the estimated bulk density further comprises using the measured bulk density measured in step d) in calibrating and adjusting estimated density values determined for the cuttings of the at least one group of cuttings scanned in e);
   g) determining if a change in trend occurs for a group of drill cutting in f);
   h) assembling a reconstituted core using a group of drill cuttings for which a change in trend was determined to occur in g); and
   i) determining at least one rock or formation parameter associated with a subterranean location in the subterranean reservoir using the reconstituted core of h).

27. A system to characterize subterranean formations, comprising:
   (a) a drill cutting collection unit for repeatedly extracting drill cuttings from a drilling fluid in groups of drill cuttings based on a time of arrival of the drill cuttings at the Earth's surface and placing the groups of drill cuttings in separate respective containers in a sequential arrangement thereof, wherein different containers are used to store different groups of drill cuttings having different times of arrival;
   (b) a device for measuring a bulk density of at least one of the plurality of groups of drill cuttings to provide a measured bulk density;
   (c) a multi-energy X-ray CT scanner having a stage capable of holding at least one of the groups of drill cuttings, and optionally including the container that holds the group of drill cuttings, and
   (d) one or more computer systems operable to i) obtain 3-D digital images of the groups of drill cuttings, ii) estimating an estimated bulk density and effective atomic number as data pairs for each of the cuttings of the at least one group of cuttings scanned in the multi-energy X-ray CT scanner of c), wherein the estimating of the estimated bulk density further comprises using the measured bulk density provided with the bulk density measuring device of b) in calibrating and adjusting estimated density values determined for the cuttings of the at least one group of cuttings scanned in the multi-energy X-ray CT scanner of c), iii) assembling a reconstituted core using at least of a portion of the at least one group of drill cuttings, iv) using the reconstituted core to determine at least one rock or formation parameter associated with a subterranean location in the subterranean reservoir, and v) output the results to at least one device to display, print, or store results of computations of (i)-(v); and
   (e) at least one device to display, print, or store results of the computations.

28. A non-transitory computer readable medium with a computer program product embodied thereon that, when performed on a processor in a computerized device provides a method for performing computations of one or more or all of the indicated steps of the method of claim 1.

* * * * *